(12) United States Patent  (10) Patent No.: US 8,688,213 B2
Ternes et al.  (45) Date of Patent: Apr. 1, 2014

(54) MANAGING CROSS THERAPY SENSING IN A MULTIPLE THERAPY IMPLANTABLE DEVICE

(71) Applicant: Cardiac Pacemakers, Inc., St. Paul, MN (US)

(72) Inventors: David J. Ternes, Roseville, MN (US); Douglas J. Brandner, New Brighton, MN (US); Ramprasad Vijayagopal, Shoreview, MN (US); Nicholas J. Stessman, Minneapolis, MN (US); William J. Linder, Golden Valley, MN (US); Keith R. Maile, New Brighton, MN (US); Abhi V. Chavan, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/660,388

(22) Filed: Oct. 25, 2012

(65) Prior Publication Data

US 2013/0138170 A1  May 30, 2013

Related U.S. Application Data

(60) Provisional application No. 61/564,084, filed on Nov. 28, 2011.

(51) Int. Cl.
*A61N 1/00* (2006.01)
(52) U.S. Cl.
USPC .......................................................... 607/18
(58) Field of Classification Search
USPC .................................................. 607/18, 3, 4
See application file for complete search history.

(56) References Cited

U.S. PATENT DOCUMENTS

| | | | |
|---|---|---|---|
| 6,169,918 | B1 | 1/2001 | Haefner et al. |
| 7,493,161 | B2 | 2/2009 | Libbus et al. |
| 7,881,782 | B2 | 2/2011 | Libbus et al. |
| 8,000,793 | B2 | 8/2011 | Libbus |
| 2005/0143785 | A1 | 6/2005 | Libbus |

(Continued)

FOREIGN PATENT DOCUMENTS

| | | |
|---|---|---|
| WO | WO-2010051389 A1 | 5/2010 |
| WO | WO-2010051475 A1 | 5/2010 |
| WO | WO-2013081747 A1 | 6/2013 |

OTHER PUBLICATIONS

"International Application Serial No. PCT/US2012/061870, International Search Report mailed Feb. 5, 2013", 5 pgs.

(Continued)

*Primary Examiner* — Robert N Wieland
(74) *Attorney, Agent, or Firm* — Schwegman, Lundberg & Woessner. P.A.

(57) ABSTRACT

An apparatus comprises a cardiac signal sensing circuit configured to sense an electrical cardiac signal from at least one of an atrium or ventricle of a heart of a subject, a therapy circuit configured to provide electrical pacing therapy and electrical autonomic neural modulation therapy to the subject, and a control circuit. The control circuit is configured to initiate delivery of the autonomic modulation neural therapy, and the control circuit includes a signal detection circuit configured to detect delivery of the autonomic neural modulation therapy in the sensed cardiac signal. The control circuit is configured to change, in response to detecting the delivery, a sensitivity of the cardiac signal sensing circuit during delivery of the autonomic neural modulation therapy.

20 Claims, 10 Drawing Sheets

(56) References Cited

U.S. PATENT DOCUMENTS

| | | |
|---|---|---|
| 2005/0149132 A1 | 7/2005 | Libbus |
| 2005/0267542 A1 | 12/2005 | David et al. |
| 2008/0103532 A1 | 5/2008 | Armstrong et al. |
| 2008/0228238 A1 | 9/2008 | Libbus |
| 2008/0288010 A1 | 11/2008 | Tehrani et al. |
| 2008/0288015 A1 | 11/2008 | Tehrani et al. |
| 2010/0185255 A1 | 7/2010 | Libbus |
| 2010/0191307 A1 | 7/2010 | Fang et al. |
| 2010/0228317 A1 | 9/2010 | Libbus et al. |
| 2010/0274321 A1 | 10/2010 | Libbus |
| 2010/0286740 A1 | 11/2010 | Libbus et al. |
| 2010/0305634 A1 | 12/2010 | Moffitt et al. |
| 2010/0318154 A1 | 12/2010 | Libbus et al. |
| 2010/0331921 A1 | 12/2010 | Bornzin et al. |
| 2011/0004262 A1* | 1/2011 | Bianchi et al. .................. 607/4 |
| 2011/0015690 A1 | 1/2011 | Ryu et al. |
| 2011/0082514 A1 | 4/2011 | Libbus et al. |
| 2011/0082537 A1 | 4/2011 | Moffitt et al. |
| 2011/0106216 A1 | 5/2011 | Libbus et al. |
| 2011/0112592 A1 | 5/2011 | Libbus et al. |
| 2011/0137360 A1 | 6/2011 | Ternes |
| 2011/0190840 A1 | 8/2011 | Shuros et al. |
| 2011/0270332 A1* | 11/2011 | Buschman et al. ............... 607/3 |

OTHER PUBLICATIONS

"International Application Serial No. PCT/US2012/061870, Written Opinion mailed Feb. 5, 2013", 7 pgs.

\* cited by examiner

MANAGING CROSS THERAPY SENSING IN A MULTIPLE THERAPY IMPLANTABLE DEVICE

CLAIM OF PRIORITY

This application claims the benefit of priority under 35 U.S.C. §119(e) of Ternes et al., U.S. Provisional Patent Application Ser. No. 61/564,084, filed on Nov. 28, 2011, the benefit of priority of which is claimed hereby, and is incorporated by reference herein in its entirety.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. Other examples include implantable devices with neural stimulation capability. The devices are typically used to treat patients using electrical or other therapy and to aid a physician or caregiver in patient diagnosis through internal monitoring of a patient's condition. Other examples of implantable medical devices include implantable diagnostic devices, implantable insulin pumps, or devices implanted to administer drugs to a patient.

The devices may include one or more electrodes in communication with sense amplifiers to monitor activity (e.g., electrical heart activity) within a patient, and often include one or more sensors to monitor one or more other internal patient parameters. In CFM devices, monitoring heart activity signals allows the IMD to detect abnormalities such as tachyarrhythmia or bradycardia. Providing multiple types of therapy to a patient under different protocols may complicate the diagnostic and therapy delivery functions of IMDs.

OVERVIEW

This document relates generally to systems, devices, and methods that provide electrical neural stimulation therapy to a patient or subject. In particular it relates to systems, devices, and methods that are compatible to deliver both electrical neural stimulation therapy and electrical pacing therapy.

An apparatus example includes a cardiac signal sensing circuit configured to sense an electrical cardiac signal from at least one of an atrium or ventricle of a heart of a subject, a therapy circuit configured to provide electrical pacing therapy and electrical autonomic neural modulation therapy to the subject, and a control circuit. The control circuit is configured to initiate delivery of the autonomic modulation neural therapy, and the control circuit includes a signal detection circuit configured to detect a signal artifact of the autonomic neural modulation therapy in the sensed cardiac signal. The control circuit is configured to change, in response to detecting the signal artifact, a sensitivity of the cardiac signal sensing circuit during delivery of the autonomic neural modulation therapy.

This section is intended to provide an overview of subject matter of the present patent application. It is not intended to provide an exclusive or exhaustive explanation of the invention. The detailed description is included to provide further information about the present patent application.

DETAILED DESCRIPTION

This document discusses systems and methods for delivering both electrical neural stimulation and electrical pacing therapy. A medical device can include one or more of the features, structures, methods, or combinations thereof described herein. For example, a cardiac monitor, a cardiac stimulator, or a neural stimulator may be implemented to include one or more of the advantageous features or processes described below. Such a device may be implemented to provide a variety of therapeutic or diagnostic functions.

Figure 1:
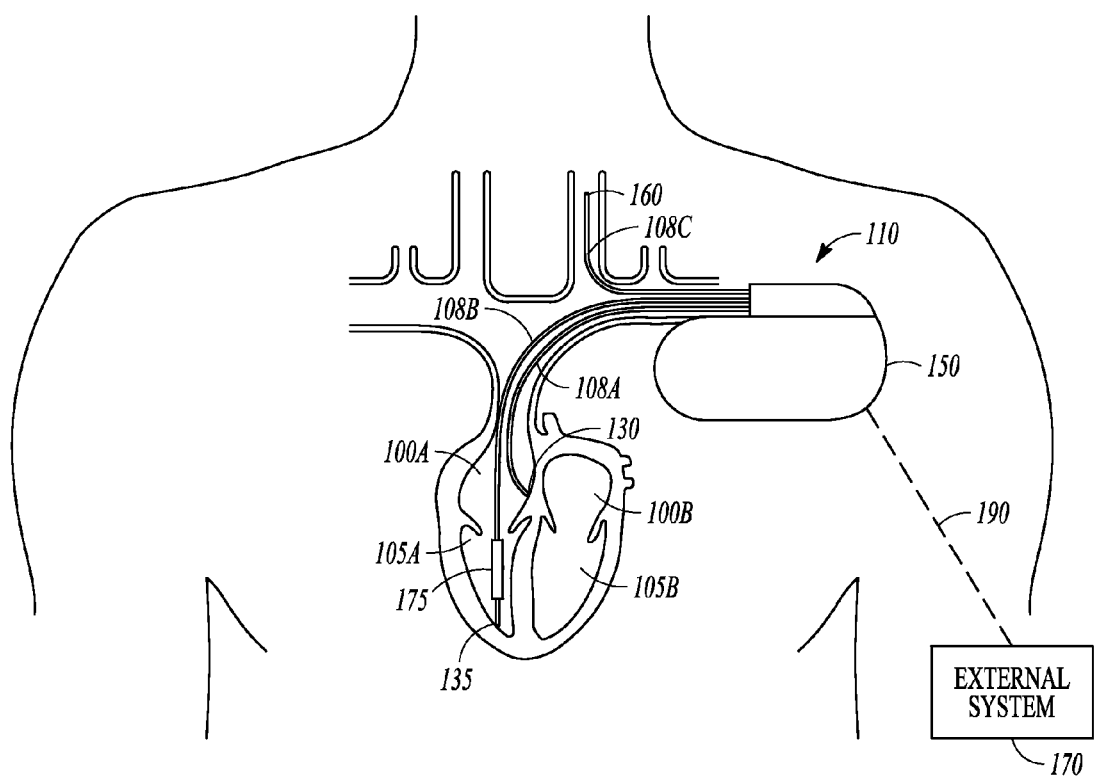
FIG. 1 is an illustration of an example of portions of a system that uses an IMD.

FIG. 1 is an illustration of an example of portions of a system that uses an IMD 110. The IMD 110 may provide cardiac pacing therapy, cardioversion or defibrillation therapy, cardiac resynchronization therapy (CRT), autonomic neural modulation therapy (AMT), or a combination of the therapies. The system also typically includes an IMD programmer or other external system 170 that communicates wireless signals 190 with the IMD 110, such as by using radio frequency (RF) signals, inductive signals, or other telemetry signals. The external system 170 can include an external device that communicates with a remote system via a network, such as a computer network or cellular phone network. In some examples, the remote system provides patient management functions and may include one or more servers to perform the functions.

The IMD 110 is coupled by one or more leads 108A-B to the heart. Cardiac leads 108A-B include a proximal end that is coupled to IMD 110 and a distal end, coupled by electrical contacts or "electrodes" to one or more portions of the heart. The electrodes typically deliver cardioversion, defibrillation, pacing, or resynchronization therapy, or combinations thereof to at least one chamber of the heart. The electrodes can be electrically coupled to sense amplifiers to sense electrical cardiac signals. Sometimes the sensing circuits and electrodes are referred to as channels. For example, circuitry used to sense signals in an atrium is referred to as an atrial sensing channel, and circuitry used to sense signals in a ventricle is referred to as a ventricular sensing channel. When direction is taken into account due to position of one or more sensing electrodes, the sensing channel can be referred to as a sensing vector.

Sensed electrical cardiac signals can be sampled to create an electrogram (sometimes called an egram). An electrogram can be analyzed by the IMD and/or can be stored in the IMD and later communicated to the external device 170 where the sampled signals can be displayed for analysis.

The heart includes a right atrium 100A, a left atrium 100B, a right ventricle 105A, and a left ventricle 105B. Right atrial (RA) lead 108A includes electrodes (electrical contacts, such as ring electrode and tip electrode 130) disposed in an atrium 100A of the heart for sensing signals, or delivering pacing therapy, or both, to the atrium 100A.

Right ventricular (RV) lead 108B includes one or more electrodes, such as tip electrode 135 and ring electrode, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to the heart. Such electrodes typically have larger surface areas than pacing electrodes in order to handle the larger energies involved in defibrillation. Lead 108B optionally provides resynchronization therapy to the heart. Resynchronization therapy is typically delivered to the ventricles in order to better synchronize the timing of depolarization between ventricles.

Lead 108B can include a first defibrillation coil electrode 175 located proximal to tip and ring electrodes for placement in a right ventricle. High energy shock therapy can be delivered using the RV coil 175 and an electrode formed on the hermetically-sealed IMD housing or can 150. In some examples, the shock therapy is delivered using the RV coil and a second defibrillation coil (not shown) located proximal to the RV coil and configured (e.g., shaped and sized) for placement in the superior vena cava (SVC). In some examples, the SVC coil and the can electrode are electrically tied together to improve defibrillation by delivering current from the RV coil 175 more uniformly over the ventricular myocardium.

The IMD 110 may also include one or more leads 108C to provide neural stimulation therapy, such as AMT. Neural stimulation can involve providing energy of constant current to nerves and is not intended to be contractile. One example of a lead to provide neural therapy is described in U.S. Pat. No. 8,000,793, filed May 23, 2008, by Libbus et al., entitled "Automatic Baroreflex Modulation Based on Cardiac Activity," which is incorporated herein by reference in its entirety.

Neural stimulation therapy leads and electrodes are designed for placement to provide therapy to specific areas of the nervous system, including the sympathetic nervous system and the parasympathetic nervous system. The sympathetic nervous system is associated with increased blood flow, heart rate, and increased skeletal muscle blood flow. The parasympathetic nervous system is associated with decreased blood pressure, heart rate, and increased digestion. Stimulating the sympathetic and parasympathetic nervous systems can affect other areas besides heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. The functions associated with the sympathetic and parasympathetic nervous systems are many and can be complexly integrated with each other.

Some IMDs can be coupled to one or more intravascular leads to stimulate nerves. Electrodes of the lead can be positioned in blood vessel proximate to a nerve trunk or nerve bundle so that electrical stimulation passes through a vessel wall to stimulate the nerve. FIG. 1 illustrates a neural stimulation lead 108C positioned in the jugular vein. The neural stimulation lead 108C includes one or more electrodes 160 to provide the neural stimulation therapy. Such a placement of electrodes may be useful for stimulation of the vagus nerve.

Figure 2:
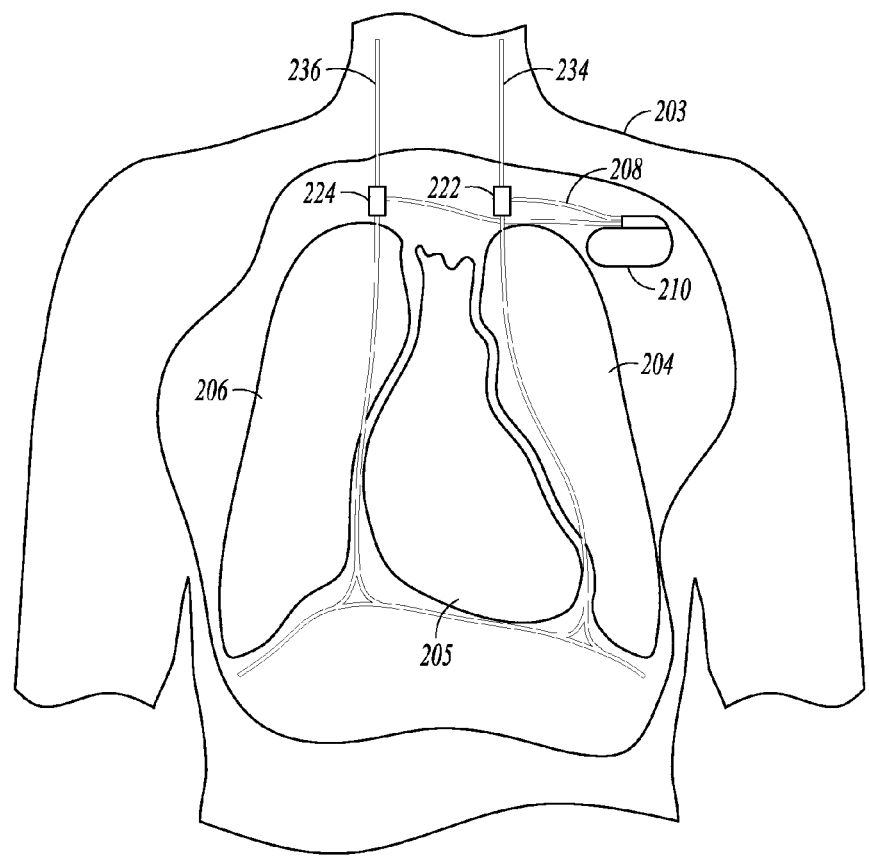
FIG. 2 is an illustration of an example of an IMD implanted in a thorax region of a patient.

In some examples, a cuff electrode is used to stimulate nerves. FIG. 2 is an illustration of an example of an IMD 210 implanted in a thorax region of a patient 203. The illustration shows the heart 205 of the subject as well as the left lung 204 and right lung 206. Also shown are representations of the left phrenic nerve 234 and right phrenic nerve 236. The IMD 210 is shown implanted in the pectoral region of the patient 203. In the example, the IMD 210 is coupled to one or more subcutaneous leads 208. In certain examples, the lead 208 includes one or more over-the-nerve cuffs 222 and 224 or collars containing electrodes for contacting a phrenic nerve.

Figure 3:
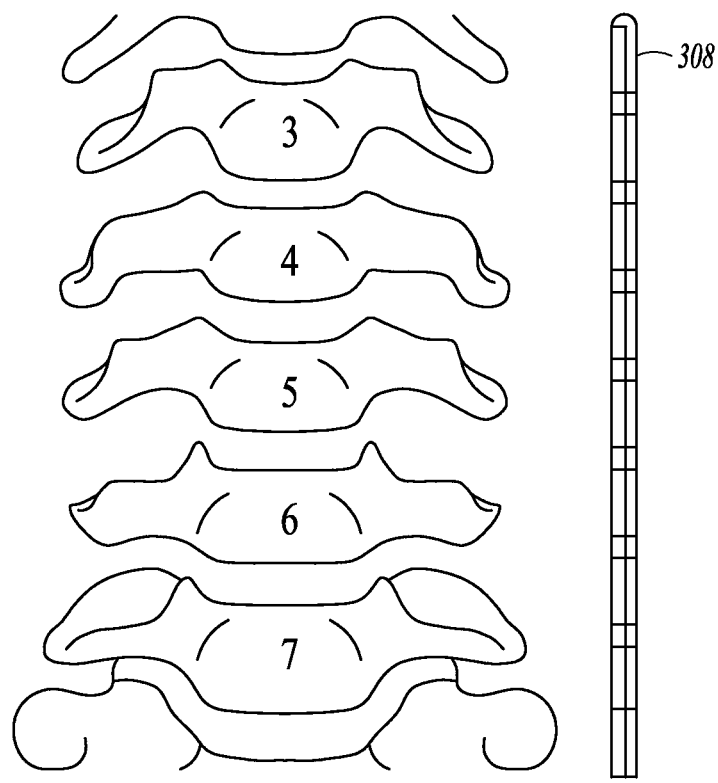
FIG. 3 shows an illustration of a multi-electrode lead configured for delivering autonomic neural modulation therapy.

FIG. 3 shows an illustration of a multi-electrode lead 308 for stimulating nerves of the spinal cord. Note that the lead and electrodes are not drawn to the same scale as the spinal cord. Other delivery sites for neural stimulation include, among others, the azygos vein, the vena cava, the carotid artery, and cardiac fat pads.

Note that although a specific arrangement of leads and electrodes are shown the Figures, the present methods and systems will work in a variety of configurations and with a variety of electrodes. An IMD can be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Other forms of electrodes include meshes and patches that can be applied to portions of the heart or nerves, or that can be implanted in other areas of the body to help "steer" electrical currents produced by IMD 110.

Figure 4:
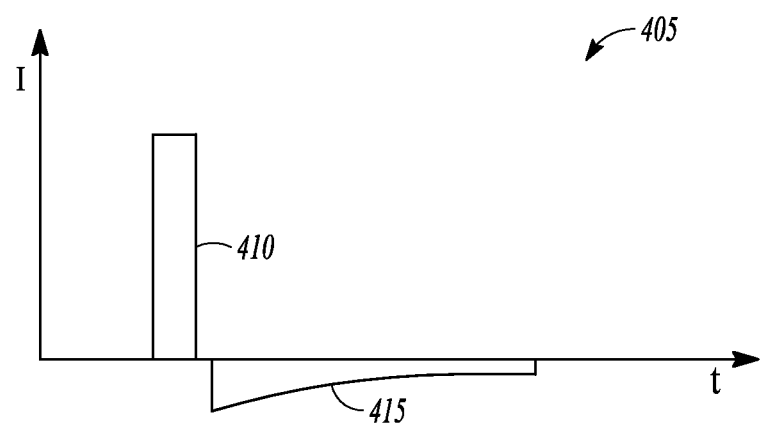
FIG. 4 shows an example of a neural modulation therapy stimulation pulse.

FIG. 4 shows an example of a neural modulation therapy stimulation pulse 405. In some examples, the neural modulation therapy stimulation pulse 405 can involve two portions. The first portion 410 is a current stimulus of constant current amplitude. The second portion 415 includes a charge-restoring stimulus. In some examples, the amplitude of the first portion 410 is programmable. Because nerves can adapt to the stimulation and the effectiveness of neural therapy may diminish over time, the neural stimulation can be modulated to mimic the effects of naturally occurring stimulation and to prevent adaptation of the nerves to the artificial stimulation. For example, during neural modulation therapy, one or more of the amplitude, frequency, wave morphology, burst frequency, and duration can be adjusted to abate adaptation.

There is a concern that providing neural modulation therapy to a patient receiving CFM therapy may introduce an electrical artifact that may be sensed by the CFM sensing circuits; this can be referred to as cross therapy sensing. For instance, in a device that provides combined AMT and CFM therapy, the circuits to provide neural stimulation may affect sensing by the CFM sensing circuits through a common electrical ground of the device or through far field sensing of the constant current stimulus and charge restoring stimulus of AMT. The device may interpret the artifact as electrical cardiac activity and may not provide CFM therapy that is appropriate. Inappropriate sensing by the CFM sensing circuits may be mitigated by adjusting the sensing parameters of these sensing circuits during delivery of AMT.

Figure 5:
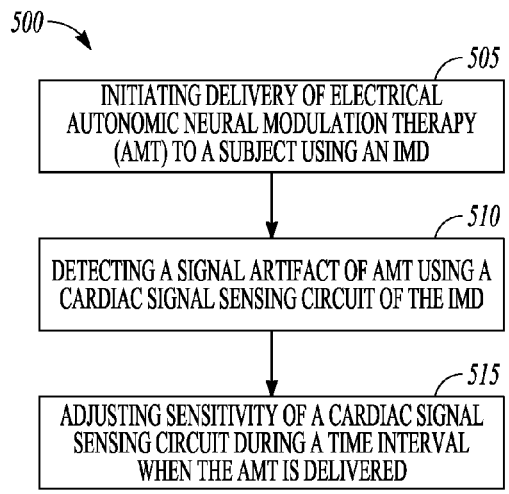
FIG. 5 shows a flow diagram of an example of a method of operating a medical device to mitigate cross therapy sensing.

FIG. 5 shows a flow diagram of an example of a method 500 of operating a medical device to mitigate cross therapy sensing. At block 505, delivery of electrical autonomic neural modulation therapy to a subject is initiated using an IMD. At block 510, a signal artifact of the AMT is detected using a cardiac signal sensing circuit of the IMD. The signal artifact may be detected by sense amplifiers of one or both of an atrial sense channel and a ventricular sense channel. In some examples, the cardiac signal is filtered to detect the frequency of delivery of the neural stimulation pulses.

At block 515, in response to detecting the signal artifact, sensitivity of a cardiac signal sensing circuit is changed during a time interval when the AMT is delivered. Changing the sensitivity of the cardiac signal sensing circuit can include one or more of changing a sensing threshold of sense amplifiers included in the cardiac signal sensing circuit, disabling operation of the sense amplifiers during delivery of the AMT, and disabling the output of the sense amplifiers.

The sensing parameters can be adjusted by a clinician when an alert is issued by the device in response to detecting the signal artifact, or the sensing parameters can be adjusted by the medical device itself in response to detection.

Figure 6:
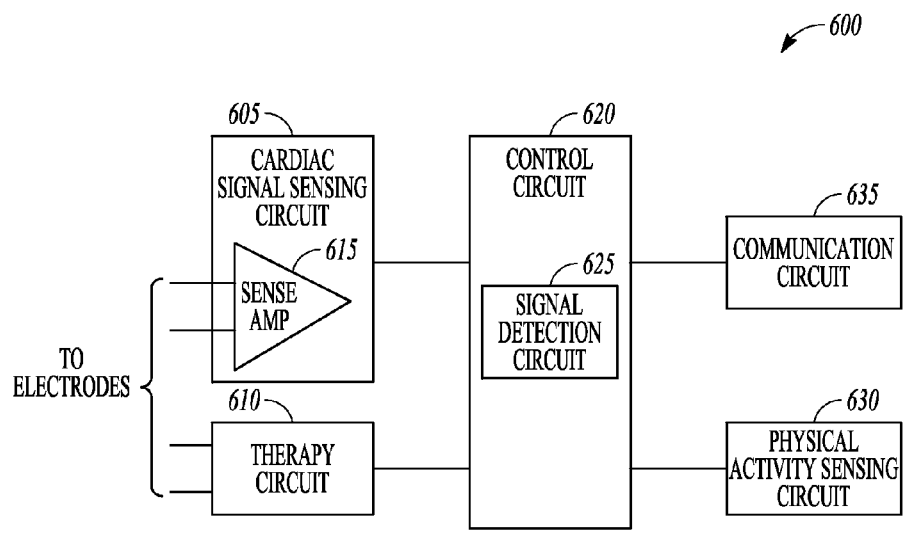
FIG. 6 shows an example of a block diagram of portions of IMD that delivers both pacing therapy and AMT, and mitigates cross therapy sensing.

FIG. 6 shows an example of a block diagram of portions of an implantable medical device 600 that delivers both electrical pacing therapy and electrical AMT and mitigates cross therapy sensing. The device includes a cardiac signal sensing circuit 605 and a therapy circuit 610. The cardiac signal sensing circuit 605 is configured to sense an electrical cardiac signal from at least one of an atrium or ventricle of a heart of a subject. The therapy circuit 610 is configured to provide electrical pacing therapy to at least one of an atrium or ventricle of the heart. The therapy circuit 610 can be electrically coupled to electrodes configured for placement in or near an atrium or ventricle to deliver the therapy. The therapy circuit 610 is also configured to provide AMT to the subject. In certain examples, electrodes coupled to the therapy and sensing circuits can be used for both sensing and therapy delivery. The device 600 may include a switch network coupled to the therapy and sensing circuits to electrically connect the electrodes to the circuits.

The device 600 also includes a control circuit 620 communicatively coupled to the cardiac signal sensing circuit 605 and the therapy circuit 610. The communicative coupling allows electrical signals to be communicated between the cardiac signal sensing circuit 605, the therapy circuit 610, and the control circuit 620 even though there may be intervening circuitry. The control circuit 620 can include a processor such as a microprocessor, a digital signal processor (DSP), application specific integrated circuit (ASIC), or other type of processor, interpreting or executing instructions in software modules or firmware modules. The control circuit 620 includes other circuits or sub-circuits to perform the functions described. These circuits may include software, hardware, firmware or any combination thereof. Multiple functions can be performed in one or more of the circuits or sub-circuits as desired.

The control circuit 620 initiates delivery of the pacing therapy (e.g., in response to detected bradycardia) and initiates the delivery of the AMT. The control circuit 620 includes a signal detection circuit 625 to detect a signal artifact of the AMT in the sensed cardiac signal. In some examples, the signal detection circuit 625 includes a peak detector and is configured to recognize when a frequency of detected peaks matches a frequency with which neural stimulation pulses are delivered as part of AMT. In some examples, the signal detection circuit 625 includes one or more filter circuits to detect a signal at the frequency of delivery of the neural stimulation. In some examples, the filter circuits are programmable to match the frequency of delivery of stimulation pulses of the AMT. In response to detecting the signal artifact, the control circuit 620 changes the sensitivity of the cardiac signal sensing circuit 605 during delivery of the AMT.

In some examples, the cardiac signal sensing circuit 605 includes at least one sense amplifier 615. The device 600 may include a sense amplifier for each sensing channel. In response to detecting the signal artifact, the control circuit 620 is configured to increase a sensing threshold of the sense amplifier 615 during delivery of the AMT.

Figure 7:
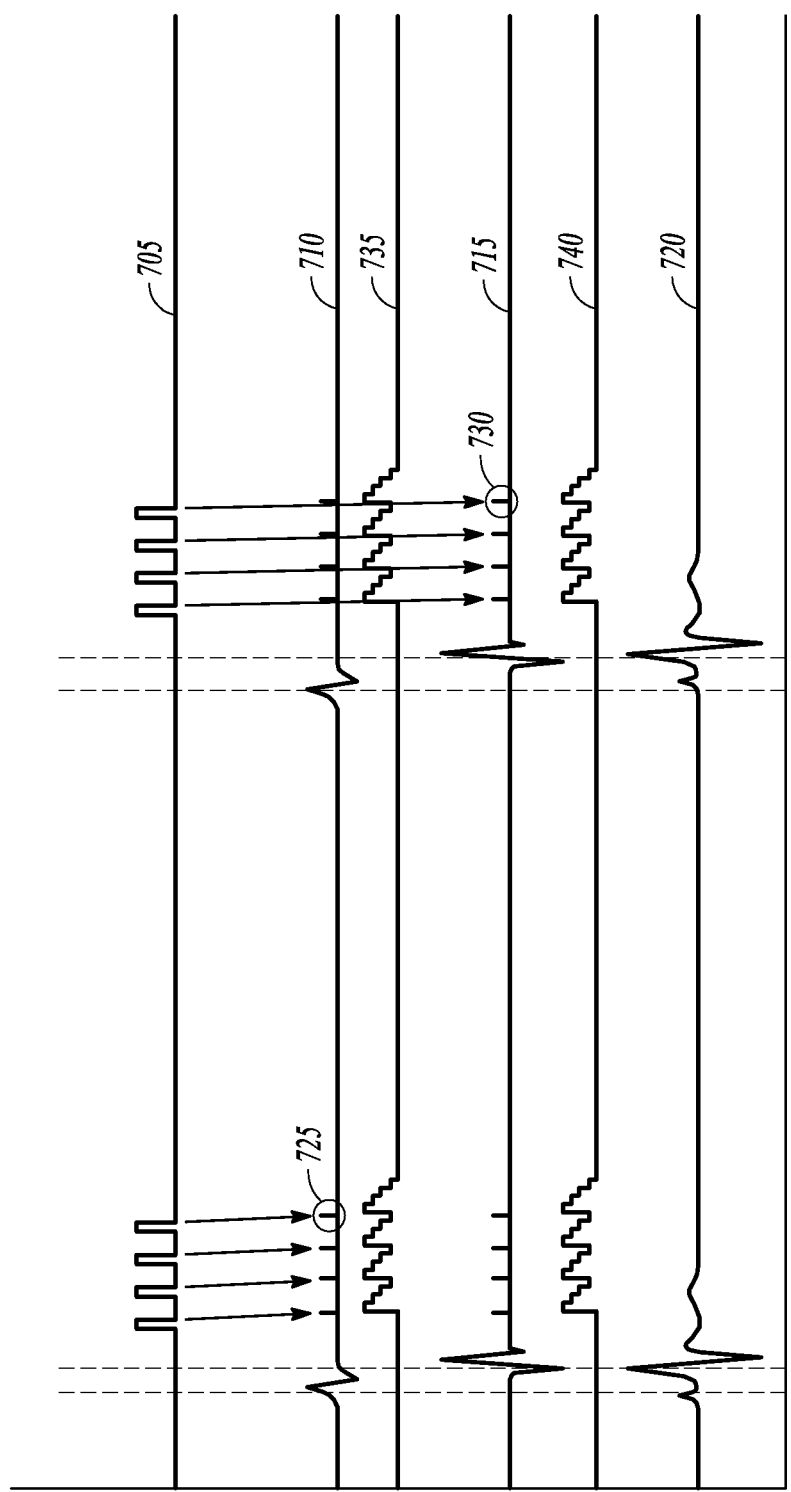
FIG. 7 is an illustration of an example of operation of a medical device to mitigate cross therapy sensing.

FIG. 7 is an illustration of an example of operation of the device 600, shown in FIG. 6, to mitigate cross therapy sensing by increasing a sensing threshold. The illustration shows six waveforms. The top waveform 705 represents an example of delivery of stimulation pulses for AMT. The example shows only four pulses to simplify the illustration. The second waveform 710 represents a filtered cardiac activity signal sensed in an atrium. Skipping to the fourth waveform 715, a representation of a filtered cardiac activity signal sensed in a ventricle is shown. The bottom waveform 720 is a representation of an electrocardiogram (EKG) corresponding to the depolarization activity in the atrium and ventricle.

The arrows from the pulses in the top waveform indicate representations of artifacts 725 in the sensed atrial cardiac signal due to AMT, and representations of artifacts 730 in the sensed ventricular signal due to AMT. It should be noted that the artifacts can be present even though the sensed signals are filtered. In response to this sensing, the device 600 can automatically reduce the sensitivity of a sense amplifier, in one or both of the atrial sensing channel and the ventricle sensing channel, to minimize the detection.

The third waveform 735 shows the control circuit 620 of FIG. 6 automatically changing the sensing threshold of the sense amplifier in the atrial channel to reduce sensitivity. The steps represent the threshold being increased to a high threshold to eliminate the artifact and then stepped down until the artifact reappears in the sensed signals. The sensing threshold is then increased to one step higher to eliminate the signal artifact with the lowest increase in the sensing threshold. The fifth waveform 740 shows a similar automatic adjustment for a sense amplifier for the ventricular sensing channel. In some examples, the sensing threshold is increased in steps until the artifact is no longer sensed in the cardiac signals. In some examples, an alert is generated when the artifact appears and a user initiates the adjustment to the sensing thresholds of the amplifiers.

According to some examples, the control circuit 620 of FIG. 6 changes the sensitivity of the cardiac signal sensing circuit 605 by disabling operation of the sense amplifier 615 during delivery of the AMT. This can be referred to as initiating a blanking period during delivery of the neural stimulation. In certain examples, the sense amplifiers are disabled during the blanking period by disconnecting one or both of the circuit connections to the sense amplifier and electrode connections to the sense amplifier. In certain examples, a sense amplifier is powered down during the blanking period.

Figure 8:
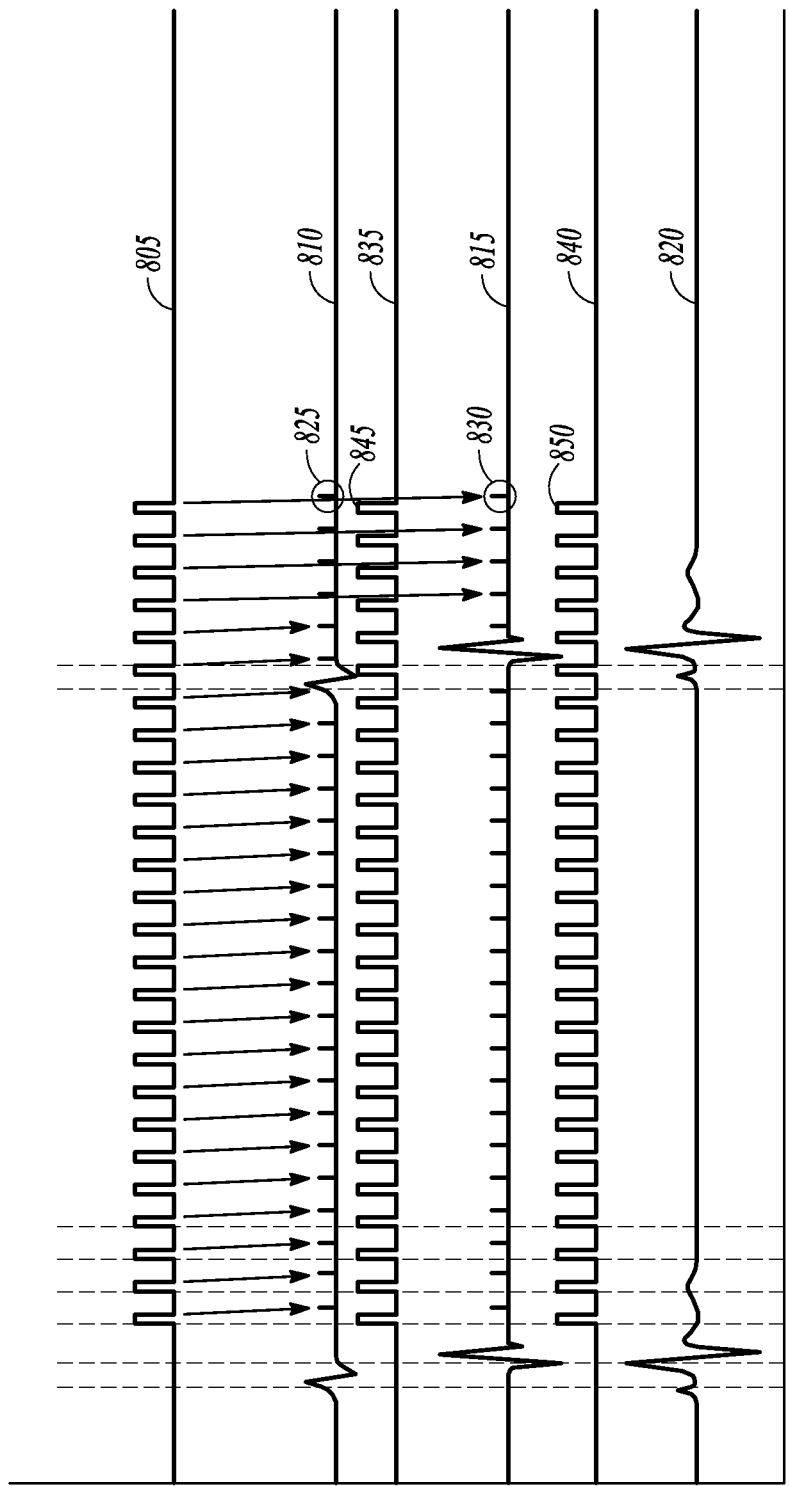
FIG. 8 is an illustration of an example of operation of a medical device to mitigate cross therapy sensing by blanking one or more sense amplifiers.

FIG. 8 is an illustration of an example of operation of the device 600 of FIG. 6 to mitigate cross therapy sensing by blanking the sense amplifier 615 during delivery of neural modulation therapy. As in the example of FIG. 7, the illustration of FIG. 8 shows six waveforms. The top waveform 805 represents an example of delivery of stimulation pulses for AMT. The example shows a burst of neural stimulation pulses that spans the duration of a cardiac cycle. The second waveform 810 represents a filtered cardiac activity signal sensed in an atrium, the fourth waveform 815 represents a filtered cardiac activity signal sensed in a ventricle, and the bottom waveform 820 is a representation of an EKG corresponding to the depolarization activity in the atrium and ventricle.

The arrows from the stimulation pulses in the first waveform 805 indicate signal artifacts 825, 830 in the sensed atrial and ventricular signals due to AMT. To eliminate sensing of the artifact by the cardiac signal sensing circuit 605, the control circuit 620 of FIG. 6 initiates blanking periods when the neural stimulation pulses are provided. The third waveform 835 shows the control circuit 620 timing a blanking period 845 in the atrial sensing channel at the time of the neural stimulation pulse. The fourth waveform 840 shows the control circuit 620 of FIG. 6 timing a blanking period 850 in the ventricular sensing channel at the time of the neural stimulation pulse. In certain examples, the blanking period begins just before the neutral stimulation pulse and lasts until just after the stimulation pulse. The blanking period may last longer to include any conduction time from the stimulation site to the sensing site. In certain examples, the blanking period is sufficient to blank the sense amplifiers during both a constant current stimulus and a charge-restoring stimulus of a neural stimulation pulse.

Figure 9:
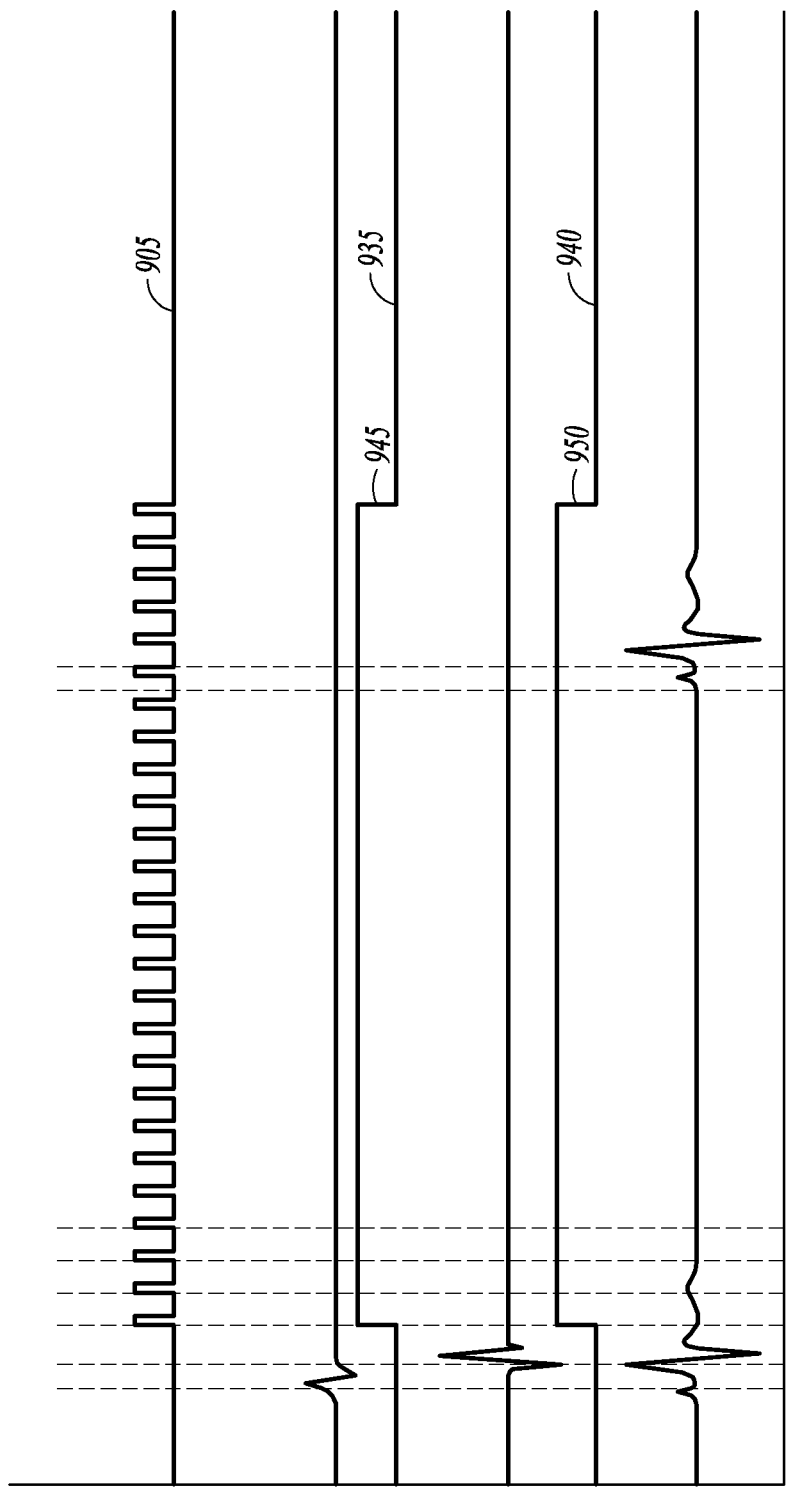
FIG. 9 is an illustration of another example of operation of a medical device to mitigate cross therapy sensing by blanking one or more sense amplifiers.

FIG. 9 is an illustration of another example of operation of the device 600 of FIG. 6 to mitigate cross therapy sensing by blanking one or more sense amplifiers. In the example, control circuit 620 establishes blanking periods 945, 950 for the entire duration of the burst of neural stimulation pulses in the top waveform 905. This means that, for this example, sense amplifiers would be disabled during the entire burst of pulses. If the burst includes many pulses, this may reduce the ability of the device 600 to detect arrhythmias. In certain examples, the control circuit 620 includes a tachyarrhythmia detection circuit that detects tachyarrhythmia when the heart rate of a subject exceeds a tachyarrhythmia detection rate threshold or heart beat interval threshold. Because imposing a blanking period for an entire burst of pulses may adversely affect the ability to detect such rates or intervals, the operation shown in FIG. 9 may be restricted to a clinical setting where a patient can be monitored directly by a clinician.

Figure 10:
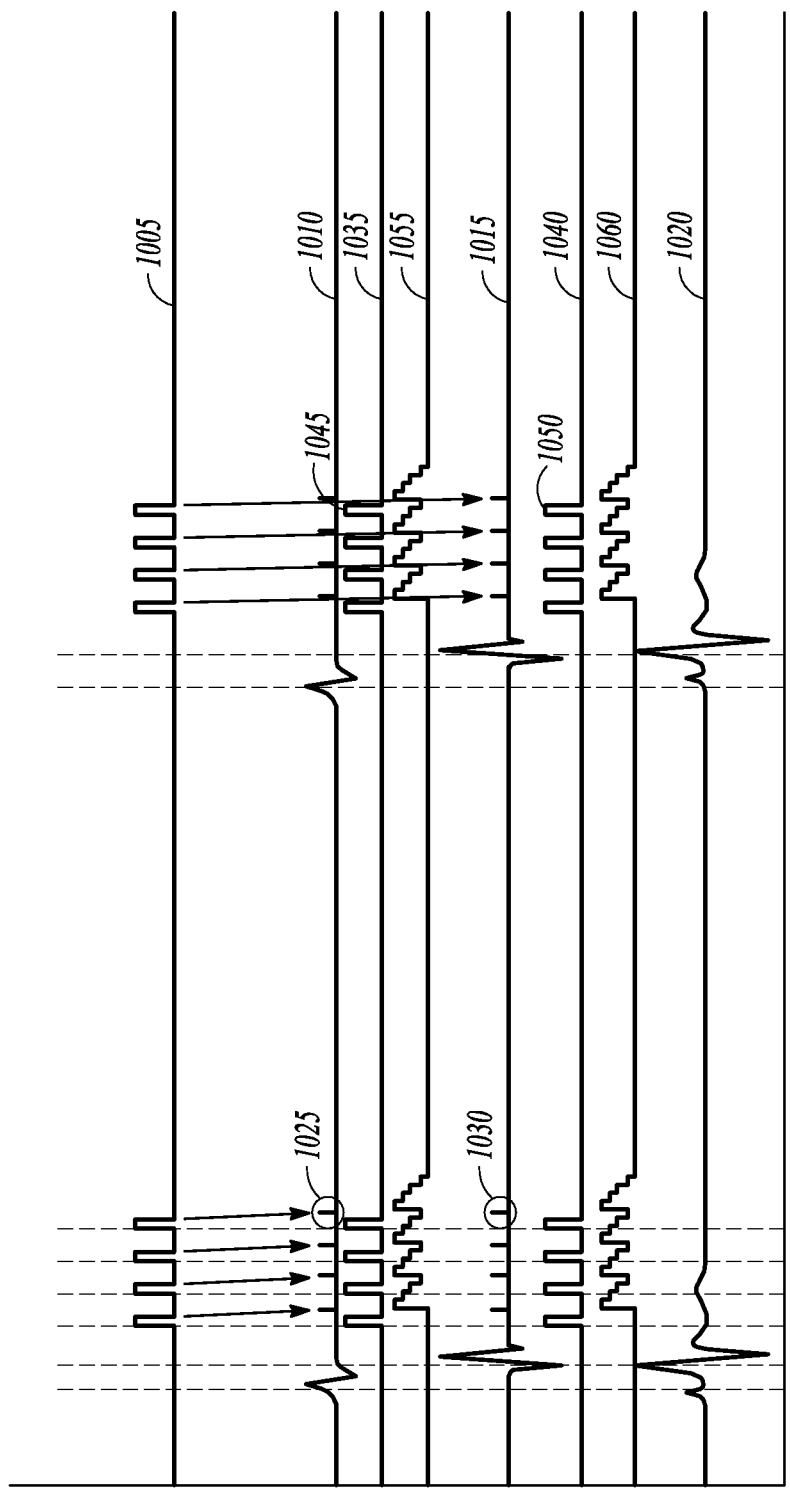
FIG. 10 is an illustration of still another example of operation of a medical device to mitigate cross therapy sensing.

FIG. 10 is an illustration of still another example of operation of the device 600 of FIG. 6 to mitigate cross therapy sensing. In the example, sensitivity of the cardiac signal sensing circuit 605 is changed by initiating both a blanking period and reducing the sensitivity of the sense amplifier 615. Neural stimulation pulses, shown in the top waveform 1005, result in signal artifacts from the stimulation being present in the sensed atrial signal shown in the second waveform 1010 and in the sensed ventricular channel shown in the fifth waveform 1015. The control circuit 620 changes the sensitivity of the cardiac signal sensing circuit 605 by establishing blanking periods 1045, 1050 (as shown in waveforms 1035, 1040) during a constant current portion of the neural stimulating pulse by increasing the sensing threshold of one or more sense amplifiers (as shown in waveforms 1055, 1060) during the charge-restoring portion of the stimulation.

According to some examples, the control circuit 620 reduces sensitivity of the cardiac signal sensing circuit 605, by establishing a refractory period in one or more sensing channels during delivery of neural stimulation pulses. During a refractory period the output of the sense amplifiers are ignored. In some examples, in response to detecting the signal artifact, the control circuit 620 disables the output of the sense amplifier 615 of the cardiac signal sensing circuit 605 during the time interval when a neural stimulation pulse is delivered.

Figure 11:
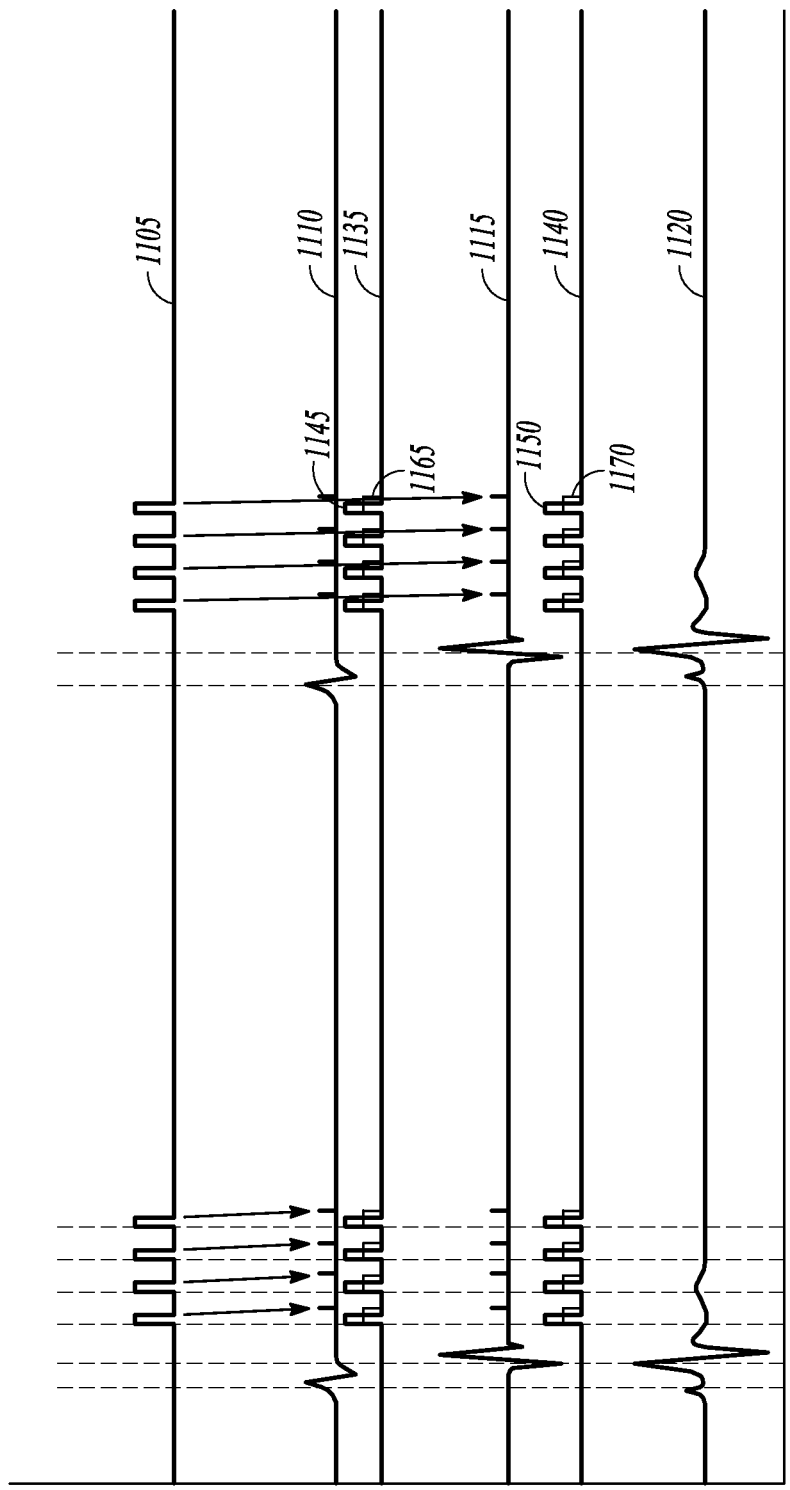
FIG. 11 is an illustration of still another example of operation of a medical device to mitigate cross therapy sensing.

FIG. 11 is an illustration of still another example of operation of the device 600 of FIG. 6 to mitigate cross therapy sensing. In the example, sensitivity of the cardiac signal sensing circuit 605 is changed by initiating both a blanking period and a refractory period during a neural stimulation pulse. As in the previous examples, neural stimulation pulses (shown in the top waveform 1105) result in signal artifacts from the stimulation being present in one or more of the sensed atrial signal shown in the second waveform 1110 and in the sensed ventricular channel shown in the fifth waveform 1115. The control circuit 620 changes the sensitivity of the cardiac signal sensing circuit 605 by establishing blanking periods 1145, 1110 (as shown by waveforms 1135, 1140) and by initiating refractory period 1165, 1170. In some examples, the duration of the blanking period can cover the duration of a constant current portion of the neural stimulation, and the refractory period can cover charge-restoring portion of the neural stimulation.

According to some examples, the control circuit 620 includes a tachyarrhythmia detection circuit (not shown) that detects tachyarrhythmia when sensing a heart rate that satisfies a specified rate detection threshold or by sensing a heart rate interval that satisfies a specified interval threshold. The control circuit 620 may initiate anti-tachyarrhythmia pacing (ATP) therapy by the therapy circuit 610 when tachyarrhythmia is detected. The device 600 may first try and convert an episode of tachyarrhythmia to spare the patient any discomfort from high-energy shock therapy. ATP can involve bursts of pacing pulses delivered at a high rate. Because of the rates involved, there is often little sensing done by the device 600 during delivery of ATP, and one or both of blanking periods and refractory periods can be imposed during an ATP pulse. Thus, the device 600 may initiate delivery of autonomic neural modulation therapy during one or both of the blanking and refractory periods during ATP. As explained herein, autonomic neural modulation therapy may drive down the heart rate of the subject. Providing neural therapy with the ATP during an episode of tachyarrhythmia may provide the added benefit of increasing the likelihood of success of the ATP.

The feature of detecting artifacts due to neural stimulation and of changing the sensitivity to minimize the detection can be enabled in a device. In some examples, the device includes a communication circuit 635 that communicates information with a second separate device such as an external system 170 of FIG. 1. The control circuit 620 receives a communication enabling the detection and sensitivity adjustment feature from the second device. In some examples, after the enabling communication is received, the control circuit 620 of FIG. 6 may further configure the feature based on the implementation of the neural therapy function and the cardiac therapy function.

As explained herein, the cardiac signal sensing circuit 605 of FIG. 6 can be communicatively coupled to implantable electrodes to sense a cardiac signal. The control circuit 620 can enable detection of the AMT in the sensed cardiac signal according to the location of the implantable electrodes. For instance, the device 600 may be configured to sense cardiac signals and to provide AMT to or near the vagus nerve of the subject. Based on this device configuration, it may be unlikely for AMT to affect cardiac signals sensed in the ventricle. Therefore, the control circuit 620 may enable detection of neural stimulation artifacts in sensed atrial signals and only enable changing the sensitivity of an atrial sensing channel according to the detection. In another example, the device 600 may be configured to sense cardiac signals and to provide AMT to a baroreceptor. The location of the baroreceptor stimulation may only effect sensing in the ventricles, and the control circuit 620 may enable detection of neural stimulation artifacts in sensed ventricular signals, and only enable changing the sensitivity of a ventricular sensing channel according to the detection.

In some examples, the control circuit 620 determines the configuration of the device 600 from the initial set up of the device 600. The device 600 may include registers or a reserved portion of memory used to identify the device configuration. The configuration may be entered into the memory or registers as part of an implant procedure, and the control circuit 620 later reads the register or memory to determine the device configuration.

In certain examples, the control circuit 620 may detect electrodes and leads attached to the device and deduce the configuration from one or both of detected electrodes and detected leads. For instance, the control circuit 620 may be able to deduce a type of implantable lead attached to the device by determining resistance of the lead or by determining a number of conducting connectors in an attached lead. The type of lead may indicate placement of one or more electrodes in an atrium or ventricle, or may indicate bipolar or unipolar sensing. These different configurations may each have different over-sensing issues, and the control circuit 620 may enable detection of neural stimulation artifacts in different sensing channels according to the determined configuration.

In some examples, the control circuit 620 enables detection of the AMT stimuli in the sensed cardiac signal according to an orientation of one or more implantable electrodes. The electrodes used to sense a cardiac signal may be a bipolar pair of electrodes. The signals caused by the neural stimulation may be directional. The detection of a signal artifact from the neural stimulation may be dependent on the bipolar electrode pair being in the direction (e.g., parallel) to the direction of signal artifact propagation rather than being perpendicular to the direction of the signal propagation. A perpendicular arrangement may not result in sufficient potential differences between the electrodes that are detected in cardiac signals. In certain examples, the electrodes used to sense a cardiac signal may be a unipolar configuration, such as an electrode placed in the right ventricle and an electrode formed on the IMD housing. This configuration may be more sensitive to signal artifacts than a bipolar configuration, and the control circuit 620 may automatically enable artifact detection when identifying a unipolar sensing channel.

In certain examples, the control circuit 620 receives a communication enabling detection of the AMT in the sensed cardiac signal from a second separate device according to a designation stored in the second device of at least one of the specified location or orientation of an implantable electrode or a type of lead.

Some electrode configurations may be more susceptible to over-sensing of the neural stimulus if the subject is exercising or otherwise physically active. According to some examples, the device of FIG. 6 includes a physical activity sensing circuit 630 communicatively coupled to the control circuit 620. Some examples of a physical activity sensor include an accelerometer and a vibration sensor. The control circuit 620 enables detection of a neural modulation therapy signal artifact in the sensed cardiac signal according to, for example, a detected level of physical activity of the subject (e.g., when the subject exceeds a specified physical activity level) in association with at least one of a specified location of a sensing electrode, a specified orientation of the sensing electrode, and a specified type of lead that includes the electrode.

In some examples, the device 600 includes a posture sensing circuit that generates a signal representative of posture of the subject. The posture sensing circuit may be integral to the physical activity sensing circuit 630 or separate from the physical activity sensing circuit 630. Examples of a posture sensing circuit include an accelerometer circuit and a tilt switch circuit. The control circuit 620 enables detection of a neural modulation therapy signal artifact in the sensed cardiac signal according to a determined posture of the subject in association with the at least one of a specified location of a sensing electrode, a specified orientation of the sensing electrode, and a specified type of lead that includes the electrode.

Figure 12:
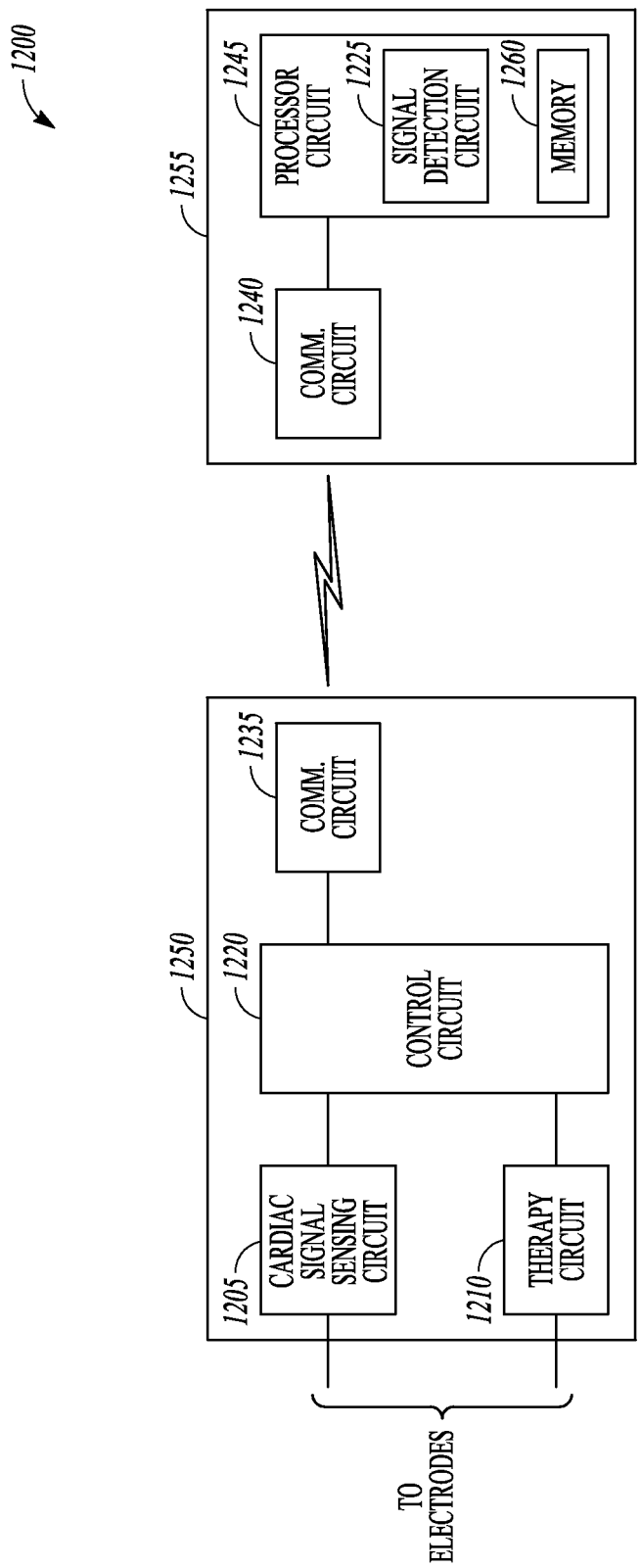
FIG. 12 shows an example of a block diagram of portions of a system that delivers both electrical pacing therapy and electrical autonomic neural modulation therapy and mitigates cross therapy sensing.

FIG. 12 shows an example of a block diagram of portions of a system 1200 that delivers both electrical pacing therapy and electrical autonomic neural modulation therapy and mitigates cross therapy sensing. The system 1200 includes an implantable device 1250 and an external device 1255. The implantable device 1250 includes a cardiac signal sensing circuit 1205 and a therapy circuit 1210 that provides both electrical pacing therapy and electrical autonomic neural modulation therapy to the subject. The implantable device 1250 also includes a communication circuit 1235 that communicates information wirelessly with a second separate device. The implantable device 1250 also includes a control circuit 1220 communicatively coupled to the cardiac signal sensing circuit 1205, the therapy circuit 1210, and the communication circuit 1235. The control circuit 1220 initiates delivery of the AMT to the subject and initiates delivery of pacing therapy to the subject.

The external device 1255 includes a communication circuit 1240 that communicates information with the implantable device 1250, including receiving a representation of sensed cardiac signals from the implantable device 1250. The external device 1255 also includes a processor circuit 1245, such as a microprocessor or DSP. The processor circuit 1245 includes a signal detection circuit 1225 that detects a signal artifact of the AMT in the representation of the sensed cardiac signal. The processor circuit 1245 communicates a change in sensitivity of the cardiac signal sensing circuit 1205 to the implantable device 1250 in response to detecting the signal artifact during delivery of the autonomic neural modulation therapy.

In some examples, the external device 1255 changes the sensitivity of the cardiac signal sensing circuit 1205 by programming an increase in the sensing threshold of one or more sense amplifiers in the cardiac signal sensing circuit 1205. The increased threshold may only be used during the delivery of the autonomic neural modulation therapy. In some examples, the external device changes the sensitivity of the cardiac signal sensing circuit by programming the control circuit 1220 to disable operation of one or more sense amplifiers during delivery of the autonomic neural modulation therapy. In some examples, the external device changes the sensitivity of the cardiac signal sensing circuit by programming the control circuit to disable an output of the sense amplifiers of the cardiac signal sensing circuit during the neural modulation therapy.

In some examples, the external device 1255 includes a memory circuit 1260 communicatively coupled to, or integral to, the processor circuit 1245. The cardiac signal sensing circuit 1205 of the implantable device 1250 can be electrically coupled to at least one implantable electrode. The processor circuit 1245 enables detection of the signal artifact in the sensed cardiac signal by the signal detection circuit 1225 according to a designation, stored in the memory circuit 1260, of one or more of a location of the implantable electrode, an orientation of the implantable electrode, and a type of lead that is coupled to the implantable device 1250 and includes the at least one electrode.

As explained herein, the control circuit 620 of FIG. 6 can include a tachyarrhythmia detection circuit. The control circuit 620 may disable delivery of AMT when an episode of tachyarrhythmia is detected by the device. In some examples, AMT is disabled during one or more of a post detection period (e.g., when the heart rate is maintained for a specified duration), a post shock period, and a specified redetection period.

In some examples, the device 600 may delay detection of tachyarrhythmia when delivering AMT. This may be useful in a clinical setting. The delay in detection may be in response to one or more of manual enabling of the neural modulation therapy, semi-automatic enabling of the neural therapy by the device, or automatic enabling of the therapy by the device. In certain examples, tachyarrhythmia is delayed a specified number of seconds (e.g., 5 sec., 10 sec., 30 sec., etc.) while the neural therapy is delivered. In certain examples, the neural therapy is duty cycled to accommodate some tachyarrhythmia detection during the neural modulation therapy. This duty cycling can include a ratio of the time that neural modulation therapy is enabled and tachyarrhythmia detection disabled to the time that neural modulation therapy is disabled and tachyarrhythmia detection enabled (e.g., a ratio of 0.2, 0.25, 0.33, 0.5, etc.).

The several examples described herein thus far address the problem of detecting AMT stimuli in sensed cardiac signals. The opposite case of sensing CFM therapy stimuli (e.g., pacing pulses) in sensed neural signals may also be a problem. In some examples, the device 600 includes a neural sensing circuit to sense electrical neural signals at one or more nerve tissue sites (e.g., the spinal cord or vagus nerve). The signal detection circuit 625 may detect a signal artifact of the CFM therapy in a sensed neural signal. In response to the detection, the control circuit 620 may reduce the sensitivity of the neural sensing circuit by any of the methods described herein during delivery of the cardiac therapy. These methods include, among other things, changing a sensing threshold of a sense amplifier of a neural sensing channel, initiating a blanking period in the sensing channel, initiating a refractory period in the neural sensing channel, or any combination of these methods. The sensitivity is reduced during the delivery of CFM therapy to the subject. The CFM therapy may include one or more of pacing therapy for bradycardia, anti-tachyarrhythmia pacing therapy (ATP), cardioversion therapy, and defibrillation therapy. Avoiding cross-therapy sensing can lead to improved reliability and efficacy in delivering device-based therapy to the subject.

ADDITIONAL NOTES AND EXAMPLES

Example 1 includes subject matter (such as an apparatus) comprising a cardiac signal sensing circuit, a therapy circuit, and a control circuit. The cardiac signal sensing circuit is configured to sense an electrical cardiac signal from at least one of an atrium or ventricle of a heart of a subject, and the therapy circuit is configured to provide electrical pacing therapy and electrical autonomic neural modulation therapy to the subject. The control circuit is communicatively coupled to the cardiac signal sensing circuit and the therapy circuit, and is configured to initiate delivery of the autonomic modulation neural therapy. The control circuit includes a signal detection circuit configured to detect delivery of the autonomic neural modulation therapy in the sensed cardiac signal. The control circuit is also configured to change, in response to detecting the signal artifact, a sensitivity of the cardiac signal sensing circuit during delivery of the autonomic neural modulation therapy.

In Example 2, the subject matter of Example 1 optionally includes a signal detection circuit configured to sense a signal artifact of the autonomic neural modulation therapy in the sensed cardiac signal. The cardiac signal sensing circuit optionally includes at least one sense amplifier. The control circuit is optionally configured to increase a sensing threshold of the sense amplifier, in response to detecting the signal artifact, during delivery of the autonomic neural modulation therapy.

In Example 3, the subject matter of one or any combination of Examples 1 and 2 optionally includes the cardiac signal sensing circuit having at least one sense amplifier, and a control circuit optionally configured to disable operation of the sense amplifier, in response to detecting the signal artifact, during delivery of the autonomic neural modulation therapy.

In Example 4, the subject matter of one or any combination of Examples 1-3 optionally includes the cardiac signal sensing circuit having at least one sense amplifier and a control circuit optionally configured to disable an output of the sense amplifier of the cardiac signal sensing circuit, in response to detecting the signal artifact, during the time interval.

In Example 5, the subject matter of one or any combination of Examples 1-4 can optionally include the cardiac signal sensing circuit configured to be communicatively coupled to at least one implantable electrode, and the control circuit configured to enable detection of the autonomic neural modulation therapy in the sensed cardiac signal according to at least one of a specified location of the at least one electrode, a specified orientation of the at least one electrode, or a specified type of lead that includes the at least one electrode.

In Example 6, the subject matter of one or any combination of Examples 1-5 can optionally include a physical activity sensor communicatively coupled to the control circuit, and the control circuit is optionally configured to enable detection of the autonomic neural modulation therapy in the sensed cardiac signal according to a detected level of physical activity of the subject in association with the at least one of the specified location of the at least one electrode, the specified orientation of the at least one electrode, or the specified type of lead that includes the at least one electrode.

In Example 7, the subject matter of one or any combination of Examples 1-6 can optionally include a communication circuit configured to communicate information with a second separate device, and the cardiac signal sensing circuit can be optionally configured to be electrically coupled to at least one implantable electrode. The control circuit can be optionally configured to receive an enable of detection of the autonomic neural modulation therapy in the sensed cardiac signal from the second device according to a designation stored in the second device of at least one of a location of the at least one electrode, an orientation of the at least one electrode, or a type of lead that includes the at least one electrode.

Example 8 can include subject matter (such as a system), or can optionally be combined with the subject matter of one or any combination of Examples 1-7 to include such subject matter comprising an implantable device and an external device. The implantable device includes a cardiac signal sensing circuit configured to sense an electrical cardiac signal from at least one of an atrium or a ventricle of a heart of a subject, a therapy circuit configured to provide electrical pacing therapy and electrical autonomic neural modulation therapy to the subject, a communication circuit configured to communicate information with a second separate device, and a control circuit communicatively coupled to the cardiac signal sensing circuit, the therapy circuit, and the communication circuit. The control circuit is configured to initiate delivery of the autonomic modulation neural therapy to the subject. The external device includes a communication circuit and a processor circuit. The communication circuit is configured to communicate information with the implantable device. The communicating includes receiving a representation of the sensed cardiac signal from the implantable device. The processor circuit includes a signal detection circuit configured to detect delivery of the autonomic modulation neural therapy in the representation of the sensed cardiac signal. The processor circuit is configured to communicate a change in sensitivity to the cardiac signal sensing circuit in response to detecting the signal artifact during delivery of the autonomic neural modulation therapy.

In Example 9, the subject matter of Example 8 can optionally include the signal detection circuit configured to detect a signal artifact of the autonomic neural modulation therapy in the sensed cardiac signal. The cardiac signal sensing circuit optionally includes at least one sense amplifier. The processor circuit can optionally be configured to program the implantable device in response to detecting the signal artifact. The programming can include at least one of increasing a sensing threshold of the at least one sense amplifier during delivery of the autonomic neural modulation therapy, disabling operation of the at least one sense amplifier during delivery of the autonomic neural modulation therapy, and disabling an output of the at least one sense amplifier of the cardiac signal sensing circuit during the time interval.

In Example 10, the subject matter of one or any combination of Examples 8 and 9 can optionally include a memory circuit communicatively coupled to, or integral to, the processor circuit. The signal detection circuit configured to detect a signal artifact of the autonomic neural modulation therapy in the sensed cardiac signal. The cardiac signal sensing circuit of the implantable device can optionally be configured to be electrically coupled to at least one implantable electrode, and the processor circuit can be optionally configured to enable detection of the signal artifact in the sensed cardiac signal according to a designation, stored in the memory circuit, of at least one of a location of the at least one electrode, an orientation of the at least one electrode, or a type of lead that is coupled to the implantable device and includes the at least one electrode.

Example 11 can include subject matter (such as a method, a means for performing acts, or a machine-readable medium including instructions that, when performed by the machine, cause the machine to perform acts), or can optionally be combined with the subject matter of one or any combination of Examples 1-10 to include such subject matter comprising initiating delivery of electrical autonomic neural modulation therapy to a subject using an implantable medical device (IMD), detecting delivery of the autonomic neural modulation therapy in a cardiac signal sensed using a cardiac signal sensing circuit of the IMD, and changing, in response to detecting the signal artifact, sensitivity of the cardiac signal sensing circuit during a time interval when the autonomic neural modulation therapy is delivered.

Such subject matter can include means for initiating delivery of electrical pacing therapy to a heart of a subject, an illustrative example of which includes a control circuit with a therapy circuit. Such subject matter can include means for detecting a signal artifact, illustrative examples of which include a signal detection circuit included in the IMD or in an external device. Such subject matter can include means for changing sensitivity of the cardiac signal sensing circuit, illustrative examples of which include a control circuit included in the IMD or a processor circuit of an external device configured to program the IMD.

In Example 12, the subject matter of Example 11 can optionally include detecting a signal artifact of the autonomic neural modulation therapy in the cardiac signal sensed by a cardiac signal sensing circuit of the IMD, and changing sensitivity of a cardiac signal sensing circuit by increasing a sensing threshold of a sense amplifier of the cardiac signal sensing circuit during the time interval.

In Example 13, the subject matter of one or any combination of Examples 11 and 12 can optionally include changing sensitivity of a cardiac signal sensing circuit by disabling operation of a sense amplifier of the cardiac signal sensing circuit during the time interval.

In Example 14, the subject matter of one or any combination of Examples 11-13 can optionally include changing sensitivity of a cardiac signal sensing circuit by disabling an output of a sense amplifier of the cardiac signal sensing circuit during the time interval.

In Example 15, the subject matter of one or any combination of Examples 11-14 can optionally include detecting a signal artifact of the autonomic neural modulation therapy in the cardiac signal sensed by the cardiac signal sensing circuit of the IMD, and adjusting the sensitivity of the cardiac signal sensing circuit using the IMD.

In Example 16, the subject matter of one or any combination of Examples 11-15 can optionally include detecting a signal artifact of the autonomic neural modulation therapy in the cardiac signal sensing channel using a remote external device configured to communicate information with the IMD, and adjusting the sensitivity of the cardiac signal sensing circuit using the remote external device.

In Example 17, the subject matter of one or any combination of Examples 11-16 can optionally include detecting a signal artifact of the autonomic neural modulation therapy delivery using at least one electrode connectable to the cardiac signal sensing channel to detect a cardiac activity signal, and enabling detection of the signal artifact in the cardiac signal sensing channel. The detection of the signal artifact of the autonomic neural therapy can optionally be enabled according to at least one of a specified location of the at least one electrode, a specified orientation of the at least one electrode, or a specified type of lead that includes the at least one electrode.

In Example 18, the subject matter of one or any combination of Examples 11-17 can optionally include enabling detection of the signal artifact of the autonomic neural therapy delivery according to, as specified by a designation entered into the IMD by a caregiver, a location of the at least one electrode, an orientation of the at least one electrode, or a lead type.

In Example 19, the subject matter of one or any combination of Examples 11-18 can optionally include enabling detection of the signal artifact of the autonomic neural therapy delivery according to, as detected by the IMD, a location of the at least one electrode, an orientation of the at least one electrode, or a lead type connected to the IMD.

In Example 20, the subject matter of one or any combination of Examples 11-19 can optionally include enabling detection of a signal artifact of the autonomic neural therapy delivery according to a detected physical activity level of the subject that exceeds a specified physical activity threshold and according to at least one of the specified location of the at least one electrode, the specified orientation of the at least one electrode, or the specified type of lead that includes the at least one electrode.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
a cardiac signal sensing circuit configured to sense an electrical cardiac signal from at least one of an atrium or ventricle of a heart of a subject;
a therapy circuit configured to provide electrical pacing therapy and electrical autonomic neural modulation therapy to the subject;
a control circuit communicatively coupled to the cardiac signal sensing circuit and the therapy circuit and configured to initiate delivery of the autonomic modulation neural therapy;
wherein the control circuit includes a signal detection circuit configured to detect delivery of the autonomic neural modulation therapy in the sensed cardiac signal; and
wherein the control circuit is configured to decrease, in response to detecting the delivery of the autonomic neural modulation therapy, a sensitivity of the cardiac signal sensing circuit during delivery of the autonomic neural modulation therapy.

2. The apparatus of claim 1,
wherein the signal detection circuit is configured to detect a signal artifact of the autonomic neural modulation therapy in the sensed cardiac signal,
wherein the cardiac signal sensing circuit includes at least one sense amplifier, and
wherein the control circuit is configured to increase a sensing threshold of the sense amplifier, in response to detecting the signal artifact, during delivery of the autonomic neural modulation therapy.

3. The apparatus of claim 1,
wherein the signal detection circuit is configured to detect a signal artifact of the autonomic neural modulation therapy in the sensed cardiac signal,
wherein the cardiac signal sensing circuit includes at least one sense amplifier, and
wherein the control circuit is configured to disable operation of the sense amplifier, in response to detecting the signal artifact, during delivery of the autonomic neural modulation therapy.

4. The apparatus of claim 1,
wherein the signal detection circuit is configured to detect a signal artifact of the autonomic neural modulation therapy in the sensed cardiac signal,
wherein the cardiac signal sensing circuit includes at least one sense amplifier, and
wherein the control circuit is configured to disable an output of the sense amplifier of the cardiac signal sensing circuit, in response to detecting the signal artifact, during the time interval.

5. The apparatus of claim 1,
wherein the cardiac signal sensing circuit is configured to be communicatively coupled to at least one implantable electrode, and wherein the control circuit is configured to enable detection of the autonomic neural modulation therapy in the sensed cardiac signal according to at least one of:
a specified location of the at least one electrode;
a specified orientation of the at least one electrode; or
a specified type of lead that includes the at least one electrode.

6. The apparatus of claim 5 including:
a physical activity sensor communicatively coupled to the control circuit, and
wherein the control circuit is configured to enable detection of the autonomic neural modulation therapy in the sensed cardiac signal according to a detected level of physical activity of the subject in association with the at least one of:
the specified location of the at least one electrode;
the specified orientation of the at least one electrode; or
the specified type of lead that includes the at least one electrode.

7. The apparatus of claim 1, including:
a communication circuit configured to communicate information with a second separate device,
wherein the cardiac signal sensing circuit is configured to be electrically coupled to at least one implantable electrode, and
wherein the control circuit is configured to receive a communication enabling detection of the autonomic neural modulation therapy in the sensed cardiac signal from the second device according to a designation stored in the second device of at least one of:
a location of the at least one electrode;
an orientation of the at least one electrode; or
a type of lead that includes the at least one electrode.

8. A system comprising:
an implantable device including:
a cardiac signal sensing circuit configured to sense an electrical cardiac signal from at least one of an atrium or a ventricle of a heart of a subject;
a therapy circuit configured to provide electrical pacing therapy and electrical autonomic neural modulation therapy to the subject;
a communication circuit configured to communicate information with a second separate device; and
a control circuit communicatively coupled to the cardiac signal sensing circuit, the therapy circuit, and the communication circuit, and configured to initiate delivery of the autonomic modulation neural therapy to the subject; and
an external device including:
a communication circuit configured to communicate information with the implantable device, including receiving a representation of the sensed cardiac signal from the implantable device; and
a processor circuit including a signal detection circuit configured to detect delivery of the autonomic modulation neural therapy in the representation of the sensed cardiac signal, and wherein the processor circuit is configured to communicate a decrease in sensitivity to the cardiac signal sensing circuit in response to detecting the delivery of the autonomic neural modulation therapy.

9. The system of claim 8,
wherein the signal detection circuit is configured to detect a signal artifact of the autonomic neural modulation therapy in the sensed cardiac signal,
wherein the cardiac signal sensing circuit includes at least one sense amplifier, and
wherein the processor circuit is configured to, in response to detecting the signal artifact, program the implantable device to at least one of:
increase a sensing threshold of the at least one sense amplifier during delivery of the autonomic neural modulation therapy;
disable operation of the at least one sense amplifier during delivery of the autonomic neural modulation therapy; and
disable an output of the at least one sense amplifier of the cardiac signal sensing circuit during the time interval.

10. The system of claim 8, including:
a memory circuit communicatively coupled to, or integral to, the processor circuit,
wherein the signal detection circuit is configured to detect a signal artifact of the autonomic neural modulation therapy in the sensed cardiac signal,
wherein the cardiac signal sensing circuit of the implantable device is configured to be electrically coupled to at least one implantable electrode, and
wherein the processor circuit is configured to enable detection of the signal artifact in the sensed cardiac signal according to a designation, stored in the memory circuit, of at least one of:
a location of the at least one electrode,
an orientation of the at least one electrode, or
a type of lead that is coupled to the implantable device and includes the at least one electrode.

11. A method comprising:
initiating delivery of electrical autonomic neural modulation therapy to a subject using an implantable medical device (IMD);
detecting delivery of the autonomic neural modulation therapy in a cardiac signal sensed by the IMD; and
decreasing, in response to detecting delivery of the autonomic neural modulation therapy, sensitivity of a cardiac signal sensing circuit during a time interval when the autonomic neural modulation therapy is delivered.

12. The method of claim 11,
wherein detecting delivery of the autonomic neural modulation therapy includes detecting a signal artifact of the autonomic neural modulation therapy in the cardiac signal sensed by a cardiac signal sensing circuit of the IMD;
wherein decreasing sensitivity of a cardiac signal sensing circuit includes increasing a sensing threshold of a sense amplifier of the cardiac signal sensing circuit during the time interval.

13. The method of claim 11, wherein decreasing sensitivity of a cardiac signal sensing circuit includes disabling operation of a sense amplifier of the cardiac signal sensing circuit during the time interval.

14. The method of claim 11, wherein decreasing sensitivity of a cardiac signal sensing circuit includes disabling an output of a sense amplifier of the cardiac signal sensing circuit during the time interval.

15. The method of claim 11,
wherein detecting delivery of the autonomic neural modulation therapy includes detecting a signal artifact of the autonomic neural modulation therapy in the cardiac signal sensed by the cardiac signal sensing circuit of the IMD; and
wherein decreasing the sensitivity of the cardiac signal sensing circuit includes adjusting the sensitivity of the cardiac signal sensing circuit using the IMD.

16. The method of claim 11,
wherein detecting delivery of the autonomic neural modulation therapy includes detecting a signal artifact of the autonomic neural modulation therapy in a cardiac signal sensed by the cardiac signal sensing circuit of the IMD;

wherein detecting the signal artifact includes detecting the signal artifact in the cardiac signal sensing channel using a remote external device configured to communicate information with the IMD; and wherein decreasing the sensitivity of the cardiac signal sensing circuit includes adjusting the sensitivity of the cardiac signal sensing circuit using the remote external device.

17. The method of claim 11, wherein detecting delivery of the autonomic neural modulation therapy includes detecting a signal artifact of the autonomic neural modulation therapy in a cardiac signal sensed by the cardiac signal sensing circuit of the IMD;

wherein detecting a signal artifact includes detecting the signal artifact of the autonomic neural modulation therapy using at least one electrode connectable to a cardiac signal sensing channel to detect a cardiac activity signal, wherein detecting a signal artifact includes enabling detection of the signal artifact in the cardiac signal sensing channel, and wherein detection of the signal artifact of the autonomic neural therapy is enabled according to at least one of:
a specified location of the at least one electrode;
a specified orientation of the at least one electrode; or
a specified type of lead that includes the at least one electrode.

18. The method of claim 17, wherein the at least one of the location of the at least one electrode, the orientation of the at least one electrode, or the lead type is specified by a designation entered into the IMD by a caregiver.

19. The method of claim 17, wherein the at least one of the location of the at least one electrode, the orientation of the at least one electrode, or the lead type is detectable by the IMD.

20. The method of claim 11, wherein detecting delivery of the autonomic neural modulation therapy includes detecting a signal artifact of the autonomic neural modulation therapy in a cardiac signal sensed by the cardiac signal sensing circuit of the IMD;

wherein detection of the signal artifact is enabled according to a detected physical activity level of the subject that exceeds a specified physical activity threshold and according to the at least one of:
a specified location of the at least one electrode;
a specified orientation of the at least one electrode; or
a specified type of lead that includes the at least one electrode.

* * * * *